US009457301B2

(12) United States Patent
Osborne

(10) Patent No.: US 9,457,301 B2
(45) Date of Patent: *Oct. 4, 2016

(54) EPTFE FILTER FOR ASEPTIC PHARMACEUTICAL USE AND METHOD OF USING

(75) Inventor: Michael W. Osborne, Louisville, KY (US)

(73) Assignee: American Air Filter Company, Inc., Louisville, KY (US)

(*) Notice: Subject to any disclaimer, the term of this patent is extended or adjusted under 35 U.S.C. 154(b) by 345 days.

This patent is subject to a terminal disclaimer.

(21) Appl. No.: 13/462,017

(22) Filed: May 2, 2012

(65) Prior Publication Data
US 2013/0186179 A1    Jul. 25, 2013

Related U.S. Application Data

(63) Continuation of application No. PCT/US2011/059796, filed on Nov. 8, 2011.

(60) Provisional application No. 61/411,279, filed on Nov. 8, 2010.

(51) Int. Cl.
B01D 39/16    (2006.01)
G01M 3/20    (2006.01)
(Continued)

(52) U.S. Cl.
CPC .......... *B01D 39/1692* (2013.01); *B01D 63/14* (2013.01); *B01D 65/102* (2013.01);
(Continued)

(58) Field of Classification Search
CPC ............. G01N 15/0826; G01N 15/08; G01N 15/082; G01N 15/088; G01N 15/0806; G01N 2015/086; G01N 2015/084; G01D 65/102; B01D 2273/18; B01D 65/104; B01D 65/10; B01D 2239/0627; B01D 39/1692; B01D 63/14; B01D 65/102; B01D 69/12; B01D 71/36; B01D 2239/0654; B01D 2323/42; G01M 3/20

USPC .......................................... 73/38, 865.9, 866
See application file for complete search history.

(56) References Cited

U.S. PATENT DOCUMENTS 3,495,440 A * 2/1970 Dorsey ................ G01N 15/065
73/28.04
4,382,378 A * 5/1983 Wadsworth et al. ............. 73/38
(Continued)

FOREIGN PATENT DOCUMENTS

JP    8136437 A    5/1996
JP    8238307 A    9/1996
(Continued)

OTHER PUBLICATIONS

Jornitz, M.W., Meltzer, T.H., "Filtration and Purification in the Biopharmaceutical Industry," Second Edition, Informa Healthcare, Drugs and the Pharmaceutical Sciences, vol. 174, pp. 627-639.
(Continued)

Primary Examiner — Marrit Eyassu
(74) Attorney, Agent, or Firm — Middleton Reutlinger; Robert H. Eichenberger; Chad D. Bruggeman

(57) ABSTRACT

A HEPA filter which utilizes spun bond scrim material and ePTFE membrane for use in an aseptic pharmaceutical filtration air handling system for installation and testing is provided. The installation and testing configuration includes the ePTFE filter with a low or ultra-low concentration of challenging aerosol in the upstream side of the filter along with a scanning device for determining the upstream concentration, all completed in situ within a pharmaceutical air handling system. At the downstream side of the ePTFE filter is positioned another scanner which may be a discrete particle scanner for calculating the penetration percentage of the aerosol through the filtering media of ultra-low concentrations. The system and configuration allows for exposure to ePTFE filtration media for certification by low or ultra-low concentrations of oil based challenging compounds.

17 Claims, 15 Drawing Sheets

(51) Int. Cl.
  B01D 63/14  (2006.01)
  B01D 65/10  (2006.01)
  B01D 69/12  (2006.01)
  B01D 71/36  (2006.01)

(52) U.S. Cl.
  CPC ............ B01D 69/12 (2013.01); B01D 71/36 (2013.01); G01M 3/20 (2013.01); *B01D 2239/0627* (2013.01); *B01D 2239/0654* (2013.01); *B01D 2273/18* (2013.01); *B01D 2323/42* (2013.01)

(56) References Cited

U.S. PATENT DOCUMENTS

| | | | | |
|---|---|---|---|---|
| 5,076,965 | A * | 12/1991 | Guelta | B01D 35/00 252/408.1 |
| 5,203,201 | A * | 4/1993 | Gogins | 73/38 |
| 5,498,374 | A | 3/1996 | Sabroske et al. | |
| 5,507,847 | A * | 4/1996 | George et al. | 55/486 |
| 5,876,489 | A | 3/1999 | Kunisaki et al. | |
| 6,269,681 | B1 | 8/2001 | Hara et al. | |
| 6,416,562 | B1 | 7/2002 | Shibuya et al. | |
| 6,435,009 | B1 | 8/2002 | Tilley | |
| 6,561,498 | B2 | 5/2003 | Tompkins et al. | |
| 6,627,563 | B1 * | 9/2003 | Huberty | 442/91 |
| 7,614,280 | B1 * | 11/2009 | Gardner et al. | 73/40 |
| 2003/0150255 | A1 * | 8/2003 | Hackett, Jr. | G01N 15/082 73/38 |
| 2008/0022642 | A1 * | 1/2008 | Fox et al. | 55/521 |
| 2008/0236305 | A1 * | 10/2008 | Masset et al. | 73/865.6 |
| 2008/0245041 | A1 * | 10/2008 | Choi | 55/524 |
| 2009/0255325 | A1 * | 10/2009 | Morse et al. | 73/38 |

FOREIGN PATENT DOCUMENTS

| | | |
|---|---|---|
| JP | 10244116 A | 9/1998 |
| JP | 2002243626 | 8/2002 |
| JP | 2007178082 | 7/2007 |
| WO | 2007015803 | 2/2007 |

OTHER PUBLICATIONS

Kahler, C.J., Sammler, B., Kompenhans, J., "Generation and Control of Tracer Particles for Optical Flow Investigations in Air"; Abstract, 420 Session 7, (2002), Exp. Fluids 33, 736-742.

Roberts, R., "The Effect of PAO Aerosol Challenge on the Differential Pressure of an ePTFE Media ULPA (Experimental) Filter," Journal of the IEST 2003 Edition, pp. 74-76.

Wikol, M. et al, "Expanded Polytetrafluoroethylene Membranes and Their Applications," Filtration and Purification in the Biopharmaceutical Industry, Second Edition, Informa Healthcare, pp. 619-640.

FDA, "Draft Guidance for Industry Sterile Drug Products Produced by Aseptic Processing—Current Good Manufacturing Practice," Aug. 2003, Pharmaceutical CGMPs, pp. 1-59.

FDA, "Draft Guidance for Industry Sterile Drug Products Produced by Aseptic Processing—Current Good Manufacturing Practice," Sep. 2004, Pharmaceutical CGMPs, pp. 1-59.

Korean Intellectual Property Office; The International Search Report and the Written Opinion of the International Searching Authority, or the Declaration; International Search Report and Written Opinion for PCT/US2011/059796; Jun. 27, 2012; pp. 1-10, Korean Intellectual Property Office, Korea.

"High efficiency air filters (EPA, HEPA, and ULPA)", European Committee for Standardization (CEN), EN-1822, parts 1 to 5 Nov. 18, 2009.

* cited by examiner

EPTFE FILTER FOR ASEPTIC PHARMACEUTICAL USE AND METHOD OF USING

CROSS-REFERENCE TO RELATED APPLICATIONS

This current application is a continuation of and claims priority to and benefit from currently pending PCT International Patent Application Serial Number PCT/US11/59796, filed on Nov. 8, 2011, which claims priority to U.S. Provisional Patent Application Ser. No. 61/411,279, filed on Nov. 8, 2010.

TECHNICAL FIELD

The present invention relates to ePTFE HEPA air filtration media used in an aseptic pharmaceutical application and air handling system and testing thereof with ultra-low concentrations of a challenging aerosol.

BACKGROUND

In most aseptic pharmaceutical cleanrooms, the final step in removing airborne particles occurs in a high efficiency particulate air (HEPA) or ultra-low penetration air (ULPA) filter that is delivering air into a controlled space. Whether the cleanroom attains and maintains its designed cleanliness class depends largely on the performance of these filters. Hence, it is a common and good practice to test the performance of all filters installed in cleanrooms to ensure that they meet the designed specifications. Filters are typically tested at the time of manufacture for overall efficiency and leaks. However, in some cleanrooms within regulated industries, such as the pharmaceutical industry, these filters are also required to be certified periodically to ensure acceptable performance during their service life. Various organizations issue recommended practices for certification of HEPA and ULPA type filters for filter leak tests and guidelines for testing and classifying such filters.

In current HEPA air filtration micro-glass media, the standard utilized in the pharmaceutical industry in aseptic processing has serious problems due to the media being fragile resulting in damage from handling, pressure, over-loading and the like. Such damage can result in leaks of the filtration media thereby compromising functionality. Leakage and damage of microglass filtration media within the pharmaceutical clean room environment is significant such that the U.S. Food and Drug Administration has issued guidelines ensuring filtration effectiveness of microglass HEPA filters by testing on a regular basis. Testing of such microglass HEPA filters in such aseptic environment is completed using high concentration oil based aerosols such as DOP (dioctylphthlate), PAO (poly-alpha olefin), DEHS (Di-Ethyl-Hexyl-Sebacat), and other similar compounds measured by traditional photometers capable of measuring such upstream and downstream concentrations. The aerosols used for such filter leak tests and challenging of these filters should meet specifications for critical physicochemical attributes such as viscosity. Leakage threshold rates of 0.01% or greater of upstream concentration from these compounds is typically the testing limit at which the pharmaceutical installation and processing area would either have to replace the filter or repair the same. The upstream concentration should always be measured at the start and end of testing.

The DOP/PAO method for aseptic pharmaceutical room filtration application and testing dates to the 1960's. Such testing of the filters in aseptic room filtration is required by regulation at least every 6-12 months by challenging the filtration media with a defined aerosol. The required aerosol challenge is maintained at a high concentration of about 20 μg PAO/L of air. A measurement of 15 μg of PAO/liter corresponds to about 20 grams of PAO/800 cfm filter/hour. For normal or standard microglass filtration media, a one-time oil based challenge compound may not negatively impact filter life of the media but may affect other structures of the filter. However, by testing at such concentrations on a regular basis, standard filter life including regular challenge testing can limit to less than five years the life cycle for microglass HEPA filtration.

In such standard challenging methodology for pharmaceutical applications and installs, a predefined challenging compound such as PAO is provided upstream of the filtration media in place. The PAO is injected into the airstream just prior to the in-situ media by nozzle or other known and calibrated device at such high concentration levels to properly determine filtration effectiveness. Such injection device creates a poly-dispersed aerosol composed of particles with light scattering mean droplet diameters in the submicron size range. A challenge concentration, as mentioned, is provided at up to about 20 μg/L which is continually introduced upstream of the filter for about three to four hours for proper certification. An upstream challenging port in the filter housing is utilized for photometric analysis. The filter face is scanned on the downstream side with the photometer probe and calculated as a percent of the upstream challenge. Scanning is conducted on the entire face of the filter to generate proper leakage analysis. Probe reading of about 0.01% as leak criteria would be indicative of a significant leak but requires, as seen, fairly high concentrations of upstream PAO which can have deleterious effects on the filtering media and HEPA performance.

Significant problems also arise in the use of PAO challenge compounds. Significant fouling of the filtration media may occur over a plurality of challenging cycles. Further, PAO has been shown to cause excessive oiling of the microglass filtering media which can result in bleed through of the challenge compound. Further, such excessive challenging can cause the filter media to become less efficient, exhibiting more of a pressure drop and correspondent higher energy costs. Additionally, the PAO challenge compound has been shown to cause damage to the filtering gel seals and gaskets resulting in potential leakage points. PAO may further cause liquification of silicon based gels or may harden or otherwise reduce the effectiveness of urethane based gel seals.

Alternative aseptic pharmaceutical filter designs have included the use of additional pre-filter requirements which work to protect the primary filtration media during normal air handling load and during challenging. Such pre-filters foul earlier in the filter life cycle thereby requiring periodic replacement and increased maintenance costs. Such pre-filtering is undesirable in that additional filtration media is therefore required, doubling of maintenance and handling requirements are expected and a lack of efficiency and increased pressure drop result.

Other problems associated with traditional micro-fiberglass HEPA filters are that they are a relatively fragile filter medium which do not react well to handling, in-place contact, vibration, humidity or chemical exposure. Such micro-fiberglass media may be readily damaged through normal handling and also have a reasonably short shelf life. Damage resulting from these various factors can cause leakage and unfiltered air to pass through the media. Further, the filter can fail normal challenging sequences as a result of such damage to the media. Thus, it is desirable to provide a filtering media that meets full HEPA filtration requirements, may be utilized in the aseptic pharmaceutical industry environment, and is more durable for handling and more reliable in remaining fully functional after required challenging sequences and during normal course of operations. However, when testing an ePTFE ULPA filter with 15 mg/m$^3$ (μg/L) of PAO, a pressure drop increase of 96% occurred in approximately 5.25 hours at 650 cfm(2). The study clearly showed PAO exposure on the order of 15 mg/m$^3$ (μg/L) was detrimental to ULPA ePTFE filters due to the drastic increase in the filter resistance (pressure drop) with time. This is due to the loading and occlusion of the pores in the ePTFE.

In addition to filter loading, when considering testing of ePTFE filters with the conventional use of PAO as a challenge aerosol, bleed through is also a potential issue. The issue of bleed through may occur when using thermally generated PAO to test ePTFE filters. This is due to the thermally generated aerosol having a 0.10-0.45 mass mean diameter which is closer to the MPPS of the filter. This creates an issue with a photometer measuring a concentration and looking for leaks at or above 0.01%. The bleed through could erroneously manifest itself as an artificially large leak or in some cases a continuous leak across the filter measuring a 0.025% or less leak rate.

It is therefore desirable to provide a fully functional HEPA filtration media which meets all requirements, is relatively durable, may be challenged appropriately to determine filtering effectiveness and leakage and which further meets all required aseptic filtration standards. It is further desirable to provide such filtration media without additional pre-filter requirements and with appropriate methodology to determine full functionality of the media and determine possible leakage points without causing fouling of the in-situ filters.

Thus, there is a need in the art to provide a fully functional aseptic pharmaceutical filter media which has associated full testing methodology, is durable, maintains HEPA filtration efficiencies and which has a long in-place filtration life.

SUMMARY

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed. It should also be appreciated that terminology explicitly employed herein that also may appear in any disclosure incorporated by reference should be accorded a meaning most consistent with the particular concepts disclosed herein.

It is therefore one aspect of the present invention to provide a replacement material and certification testing for leak size and detection of aseptic clean room filtering media which utilizes a significantly lower resistant media, thereby substantially reducing energy costs.

It is further desirable to provide a method for certification and testing of media in such conditions using ultra-low concentrations of PAO and a means for detection of said ultra-low concentrations downstream of the filter to determine leak size and filter condition.

In another aspect of the present invention, it is desirable to provide a more efficient alternative to micro-fiber glass filtering media in such an environment.

It is therefore one aspect of the present invention to integrate ultra-low level PAO testing and challenging of ePTFE HEPA filtration media in an aseptic cleanroom environment. It is a further aspect of the present invention to provide an ePTFE bi-component filtration media which may be appropriately tested and certified on a regular basis for efficiency and leakage with an aerosol without fouling of the ePTFE membrane or filter media.

In some embodiments, the filter system and media of the system described herein includes a dual layer bi-component media of spun-bond material, the bi-component material being a combination of PET and PE with a total weight of about 80 GSM for both layers and a combined stiffness of about at least 400 Gurley.

In various embodiments, the dual layer of bi-component material may include a density of about 8 PPI with an average pleat height of about 25 to about 55 mm. Optimally, in many embodiments, the pleat height will be about 35 mm.

In some filters, the pleat separators can be a clear poly-alpha olefin separator bead applied in between each pleat to assure pleat separation and spacing. In other filters and embodiments, the pleats can be formed by embossing a pattern in the media that assures pleat separation and spacing.

In other aspects, the specially formulated ePTFE membrane may be about 8 to about 15 microns and preferably about 10 microns.

In some aspects, the bi-component filter material may be laminated with the ePTFE membrane at about 160 degrees C.

In various aspects, the resulting material can be rolled and then later pleated as set forth for insertion into air filter assemblies which can include metal gel seal, neoprene or knife edge frame types.

Upon insertion of the ePTFE HEPA filter at an installation, some aspects set forth herein can include regular certification and leakage testing by use of ultra-low PAO challenging aerosol at down to about 0.010 μg PAO/L of air and up to about 6.0 μg/L. More particularly and alternatively, an ultra low concentration of about 0.3 μg/L PAO to about 0.5 μg/L with a combination of particle sizes of about 0.3 μm to about 0.5 μm particle count sizing. Correspondingly, a discrete particle counter can be combined with the aerosol generator for challenging and leakage testing, in various embodiments, which can include a counter able to test at 0.5 μm to about 0.3 μm or smaller μm channel size.

In other embodiments, microspheres (polystyrene latex) may be generated as a challenging material and read on the downstream side of the filtering membrane using a particle counter to similarly determine leakage and filter efficacy. In various examples, microspheres sized from 0.12 and up to 0.30 μm can be utilized. Similar testing and challenging concentrations can as well include challenging measurements of $20 \times 10^6 \geq 0.3$ μm particles per ft$^3$ PAO to about $7 \times 10^6 \geq 0.5$ μm particles per ft$^3$ PAO.

Generally, in the various examples and embodiments provided, a filter and testing methodology is provided wherein a specialized ePTFE HEPA filter may be utilized and appropriately challenged for certification purposes while maintaining the efficiency and efficacy of the filtering media. Usage of the various embodiments described herein provides alternative testing and certification methodology for clean room application of ePTFE filtering media without the significant drawbacks of high volume PAO aerosol testing previously seen in the art.

It is therefore one aspect of the present invention to provide a system for installation and testing of ultra-low concentration challenging PAO or other type of aerosol upstream of an ePTFE HEPA filter for use in aseptic pharmaceutical clean rooms wherein the challenging concentrations of the PAO or other aerosol is less than about 1.0 µg/L air challenge aerosol with an associated low or ultra-low concentration upstream scanner, in conjunction with a downstream ultra-low concentration particle detector or other scanner for determination of downstream concentration of the challenging aerosol. To measure a 0.01% leakage rate based on a 1.0 µg/L down to about 0.3 µg/L and further down to about 0.1 µg/L and lower upstream challenge aerosol concentration, a photometer or detector downstream must be sensitive and accurate for measuring a leakage rate of 0.01% upstream PAO challenge concentrations, or a downstream concentration of less than 0.001, 0.00003 and further down to about 0.00001 µg/L and lower concentrations. Such low challenging concentrations thus results in significantly extended challenge life of the filtering media, i.e. total exposure time of the ePTFE media to the PAO, oil based or other type of challenging aerosol. Such low exposure times significantly extend the testing and installation life of an ePTFE filter media installation requiring regular leakage certification.

Various methods of use include installing an ePTFE based filter into an aseptic pharmaceutical installation, introducing an ultra-low challenge concentration of a challenging aerosol, measuring the upstream low concentration at the upstream filter face of the aerosol, detecting the ultra-low concentrations of aerosol on the downstream face of the ePTFE filter by utilization of a discrete particle counter or photometer and calculating the total ultra-low leakage rate of the challenging aerosol at the downstream face of the filter.

In other embodiments, the method further incorporates installation and leakage testing of ePTFE filtration media in an aseptic filtration environment including installing a filtration media having an upstream spun bond scrim material and a downstream spun bond scrim material, interposing an ePTFE membrane between the upstream scrim material and the downstream scrim material, injecting into the upstream air a low or ultra-low concentration of challenging aerosol at or below 1.0 µg aerosol/L air down to about 0.10 µg aerosol/L air or below, measuring the concentration of the challenging aerosol at the upstream spun bond scrim material, allowing the challenging aerosol to penetrate through the ePTFE membrane, measuring the concentration of said challenging aerosol by particle detection at the downstream spun bond scrim material to a value as low as from 0.3 to 0.1 µg aerosol/L air or lower to 0.01 ug/L, calculating a leakage detection of the challenging aerosol to values down to a leakage threshold rate of about 0.01% of the upstream challenging concentration.

Various methods may further include installing a downstream particle scanner for measuring the concentrations at the downstream spun bond scrim material. The scanner may be a discrete particle scanner. In other variations, the method may further comprise transmitting the concentration measurements of the upstream scanner to a computer, transmitting the concentration of measurements of the downstream scanner to a computer, calculating a leakage percentage of the challenging aerosol through the ePTFE filtration media over a predetermined period of time.

Alternatively, various methods may further include installing a communication link between an upstream scanner and a downstream scanner, transmitting the concentration measurements of the upstream scanner to a reading device, transmitting the concentration of measurements of the downstream scanner to the reading device, calculating a leakage percentage of the challenging aerosol through the ePTFE media by a processor, and reporting the calculated percentage to a user.

These and other variations of the system and method for leakage detection in an ePTFE filter media for use in an aseptic pharmaceutical environment are further described herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 12 is a flow chart detailing the machinery and steps involved in creating an ePTFE filtration media having an upstream scrim, a downstream scrim and an ePTFE membrane laminated there between;

DETAILED DESCRIPTION

Figure 1:
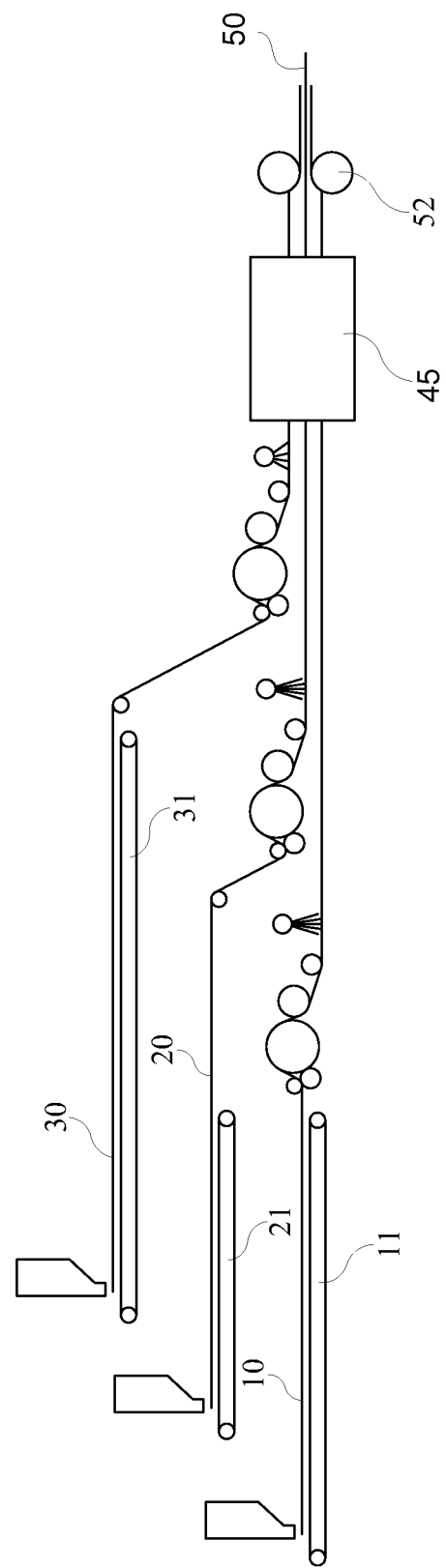
FIG. 1 is a side view of one embodiment for machinery which makes the filter media described herein.
Figure 2:
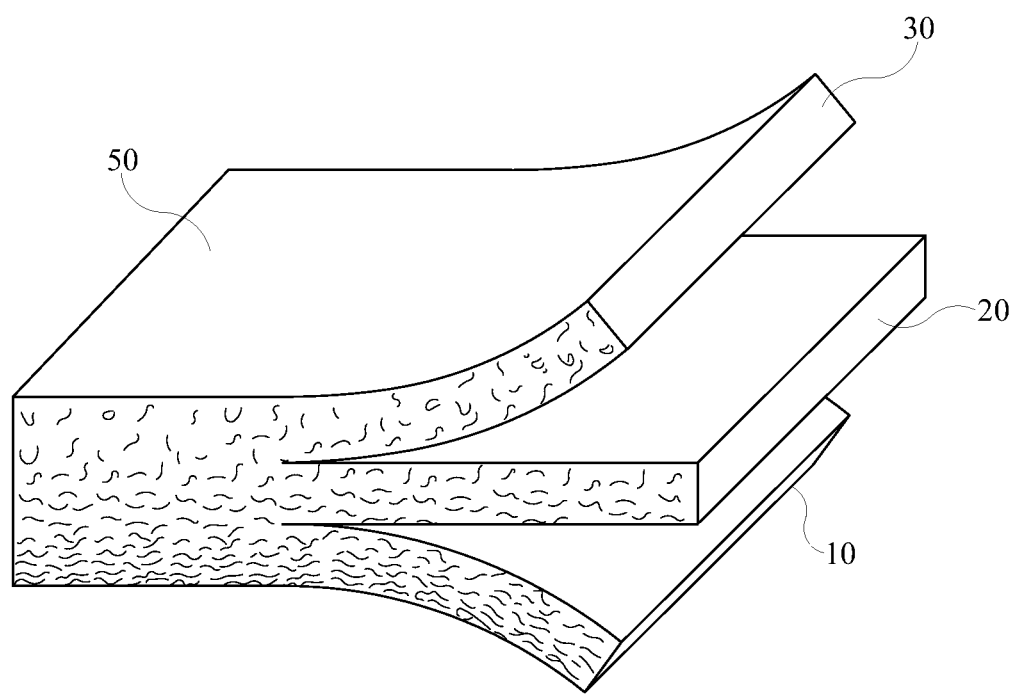
FIG. 2 is a sectional view of the filter media according to one aspect of the present invention.

In the following detailed description, for purposes of explanation and not limitation, representative embodiments disclosing specific details are set forth in order to provide a thorough understanding of the claimed invention. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the claimed invention. For example, the aspects of a fluid filtering system disclosed herein are described in conjunction with a plurality of filter structures that are arranged in a specific fashion and that interface with other structural components of the fluid filtering system in a specific fashion. However, one or more aspects of a fluid filtering system described herein may be implemented with filter structures arranged in alternative configurations and/or with filter structures that interface with other structural components of the fluid filtering system in alternative ways. Also, for example, as described in additional detail herein, filter structures disclosed herein may vary in one or more respects from those specifically depicted herein. Implementation of these and other variations is contemplated without deviating from the scope or spirit of the claimed invention.

In FIGS. 1 through 10, various aspects of an exemplary filter structure 118 are depicted. In the various figures, several embodiments for production and assembly of the filter media and system described herein are shown. In other figures, embodiments of the machinery for manufacturing the multilayer HEPA filter are also depicted. In still other figures and embodiments, multiple aspects of a separator used for separation of the filtering pleats are also shown and depicted. The embodiments and variations of the filters herein are able to be used in combination with the testing and challenging methodology described herein to ensure filter and seal integrity. Such testing methodology provides the ability to challenge a HEPA ePTFE filter with low volume or ultra-low volume PAO or PSL's at various amounts and concentrations while also detecting possible leakage or damage to the filtering media. Such low or ultra-low volume and concentration challenge methodology combined with an ePTFE HEPA filter ensures low concentration exposure of PAO to the upstream side of the ePTFE filtering media by a selectably controllable nozzle or PSL's. Further, concentrations and leakage determination can be calculated by a particle counter positioned to scan the filtering media surface on the downstream side of the media.

By low and ultra-low concentrations of challenging aerosol, it is meant that the concentrations are about 1.0 µg aerosol/L air down to about 0.01 µg aerosol/L air and below for ultra-low volumes, as well as detection of concentrations at an ultra-low values by a factor of 100 (0.01%) indicating a detectable concentration of down to about 0.000001 µg aerosol/L. air. Thus, downstream ultra-low particle detection is required to be able to detect such low concentrations of challenging materials using, among other devices, a discrete particle counter.

As set forth herein, a method for use and testing of an ePTFE filtering media is provided. The ePTFE HEPA filter is suitable for use in an aseptic pharmaceutical environment and is combined with a routine testing challenge which ensures filter integrity. As summarized herein, several embodiments of the filter and testing methodology include a HEPA filter having a bi-component scrim wherein an ePTFE membrane is laminated between a top and a bottom bi-component layer. The HEPA ePTFE filtering material may be utilized with a corresponding PAO testing and challenging regimen which includes low centration PAO exposure to the air stream with the HEPA ePTFE filter in place while utilizing a particle counter to determine corresponding pass through of the PAO challenge material. Detection of even minute particles of PAO by the particle counter may indicate damage to the filter which may then be correspondingly repaired or replaced as needed. By utilizing a pairing of an ePTFE filter with an ultra-low concentration PAO challenge and a particle detector, use of HEPA ePTFE without fouling of the membrane by the PAO is accomplished.

As shown in FIG. 1, an exemplary machine for combining the bi-component layers 10 and 30 which are moved by belts 11 and 31 with the ePTFE membrane 20 is shown. Belt 21 feeds the specially formed membrane 20 sandwiched between two 40 gsm spunbond bi-component non-woven layers 10 and 30. The upper and lower layers 30 and 10, respectively, can be of various types of filtering media for lamination with ePTFE membranes that are known in the industry and the specific types of media utilized herein are not to be deemed limiting. A HEPA ePTFE bi-component filter as described herein may exhibit an initial air flow resistance value which is 50% less than a standard HEPA glass media filter typically used in such environment. Such filter may be tested for certification in some embodiments using the methodology described herein utilizing ultra-low concentrations of PAO or microspheres along with a discrete particle counter to determine leak size and leakage indicative of damage to the filtering media.

The two spunbond layers 10 and 30 may be selected to provide a total weight of about 80 gsm combined such that each individual layer may be more or less than the exemplary 40 gsm layer as needed for the specific application and to provide a good laminating surface for bonding with the ePTFE membrane 20. The bi-component layers may also be selected to provide a combined stiffness of at least about 400 Gurley. These bi-component materials may be selected from many known members but, in various embodiments, polyethylene and PET may be combined to form the spunbond bi-component material. As indicated, an exemplary specification for the scrim may be a PE/PET bi-component spunbond scrim for lamination purposes. In various embodiments, each layer may have a basis weight of 40±3 g/m2 and a thickness of 0.25±0.05 mm. An exemplary air permeability is greater than about 350 cfm with a tensile strength of MD>100 N/5 cm and CD>30.

Figure 3:
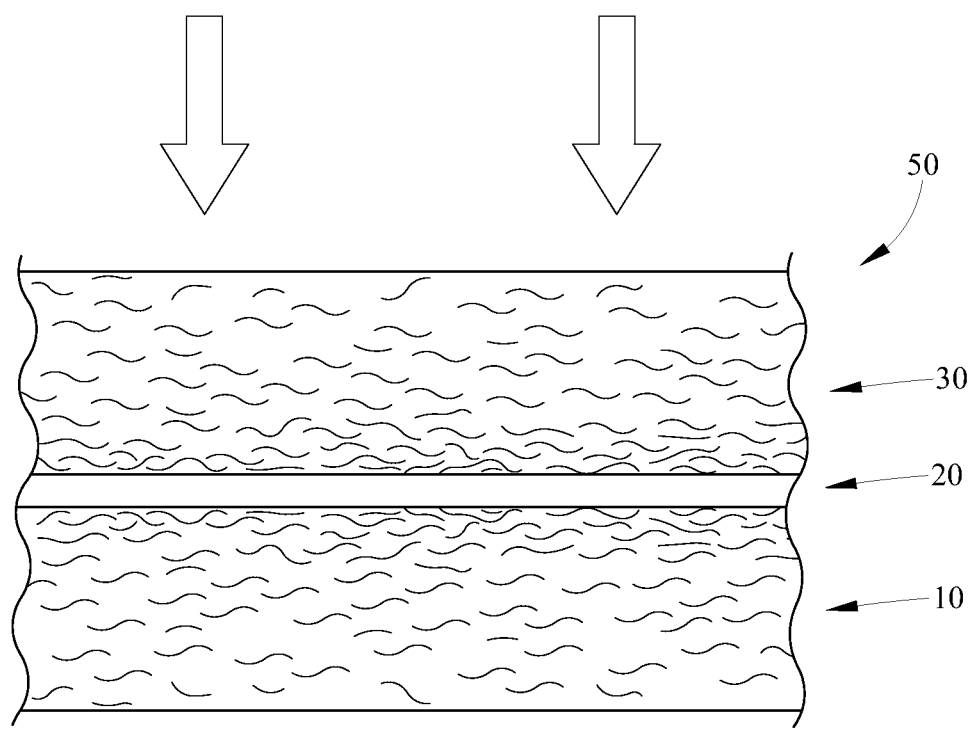
FIG. 3 is a close up side view of the filter media shown in FIG. 2.

Returning to FIG. 1, bi-component layers 10 and 30 are fed by belts 11 and 31 to a laminating station or combination area 45 wherein ePTFE membrane 20 is fed by belt 21. Combined filtering media layer 50, shown in FIGS. 1, 2, 3, and 5A, depicts the bi-component layers laminated to the ePTFE membrane 20. As seen in FIG. 1, laminating station 45 bonds the membrane to the layers 10 and 30 at a temperature of about 165 C to about 175 C at a speed of about 20 to 30 m/min. Pressure rollers 52 are also provided to ensure proper laminating of the two layers 10, 30 with the membrane 20 after application of the laminating heat. Similarly, FIG. 2, while not shown to scale, depicts the membrane layer 20, which is fed from a roll after being previously mixed and formed, in between the lower and upper scrim layers 10 and 30, respectively. Once heat treated and properly laminated by the laminating station 45 and rollers 52, the combined ePTFE filtering media 50 is depicted in FIG. 3 with upper and lower layers 30, 10 positioned opposite each other and heat laminated/bonded with the membrane 20.

In the present embodiment, the combined filtering media 50 is a HEPA filter mat having fiber diameters of between 0.5 and 2.0 micrometers. As is known, HEPA filters remove at least 99.97% of the airborne particles 0.3 µm (micrometers) in diameter. While the spunbond scrim layers do not provide membrane-like entrapment filtration, they are combined with an actual membrane layer 20 where particles are actually trapped by the tendrils of the ePTFE membrane material. The ePTFE membrane 20 depicted herein provides unique characteristics in combination with the scrim layers as well as the specific testing and challenging methodology using ultra-low PAO concentrations preventing fouling of the membrane by the PAO and maintaining filter efficiency even after multiple certification challenges.

Figure 12:
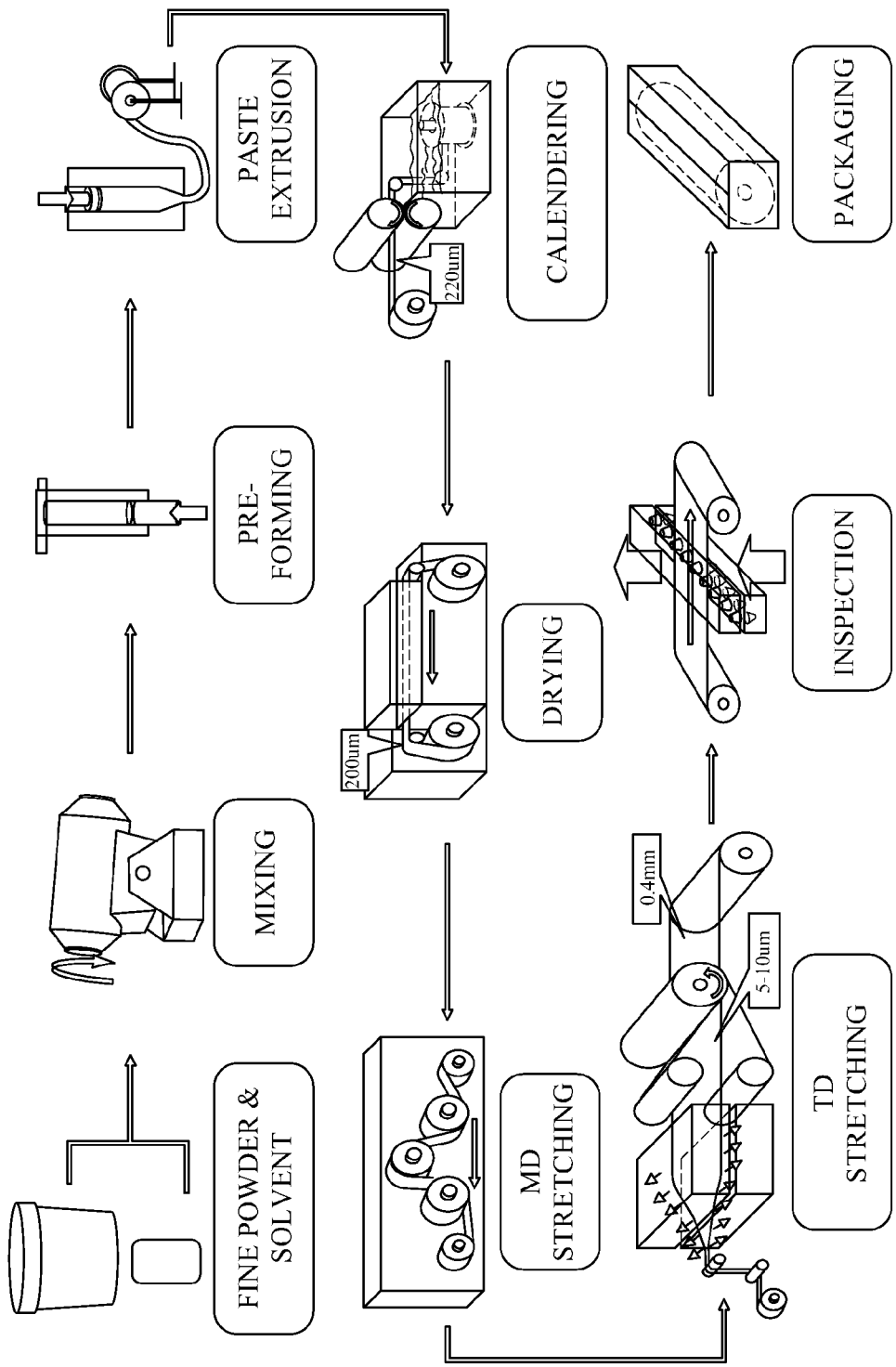

With reference now to FIG. 12, the specialized ePTFE membrane 20 utilized herein is created from a fine powder PTFE material, for example a powder from Daikin called Polyflon PTFE F-135. The fine powder utilized has a standard specific gravity of about 2.149 to about 2.165 and a bulk density of about 0.42 to about 0.54 g/ml. The fine powder further has a particle size distribution of 400-650 µm.

The fine PTFE fine powder is then mixed with an oil at a ratio of about 33% into a doughy billet. The mixing oil may be IP Solvent 2028 with a viscosity of 3.01 m·Pa·s/at 20 degrees C. and a density of 213 to about 262 g/cm3 at about 15 degrees C. This mixture is brought to a boiling point at about 213 to about 262 C with a mixing time of about 10 minutes. Once the material is thoroughly mixed, it can be stretched into a membrane or film through both TDO and MDO stretching. Initially, an MDO stretch is accomplished at a 5:1 ratio and at a temperature of about 50 degrees C. Three rollers are utilized in MDO stretching, each roller heated to about 250 degrees C. After completion of the MDO stretch, a TDO stretch is accomplished at a ratio of about 30-50 to 1. The membrane is preheated at a temperature of about 200/200 degree C., a stretching temperature of 300/300 degree C. and a heat set temperature of about 370/500 degrees C. Once the membrane is formed, it can be rolled for later use and combination within a scrim layer for formation of an ePTFE filter material.

An exemplary process for creation of the ePTFE membrane for use in the filter media and method steps discussed herein is shown in FIG. 12. As can be seen, the fine powder solvent is combined with mixing oil and finely mixed. The paste is then pre-formed and then extruded through an extruder for calendering to a roll of membrane at about 220 µm. Once it is calendered, a roll of ePTFE membrane is formed which may then be sent to a dryer for adequate drying so that the membrane may be stretched as necessary to prepare for lamination at an appropriate thickness. Variant TDO/MDO stretching may be imparted onto the ePTFE membrane such that after lamination to the scrim material, including in the varying embodiments of a bi-component scrim discussed herein, the combined media exhibits the necessary and desired pressure drop and efficiency appropriate for the desired application.

After completion of the TD stretching as depicted in FIG. 12, the membrane 20 has a thickness of between about 6 to 10 µm prior to combining with the upper and lower bi-component scrim layers 30, 10 as shown. The combined HEPA ePTFE media exhibits a total thickness of about 0.40 mm with a range of between 0.25 and 0.55 mm. Further, the basis weight, in varying embodiments, is shown to be about 81 g/m$^2$ with a range of between about 76 and about 86 g/m$^2$. Further, the average pressure drop of the combined media produced with the ePTFE membrane made and applied as set forth herein is about 11.73 mm H$_2$O with a range of about 10.20 to about 13.26 mm H$_2$O.

Referring again to FIG. 1 there is shown an example of an alternative embodiment and machine designed for combination of the dual scrim layers and the ePTFE membrane 20. After combining the multiple layers together, the combined filtering material 50 may be fed into a laminating machine 45 as discussed herein. The lamination speed for bonding of the membrane to the bi-component layers 10, 30 is approximately 20-30 m./min. and results in a combined HEPA ePTFE filtering media having a pressure drop of about 100-150 Pa. and a related efficiency of greater than 99.94%. Such ratings are exhibited with a testing condition of air stream velocity of 0.053 m/s with a silica aerosol.

In some embodiments the ePTFE membrane 20 may be a single or include multiple layers with a minimum thickness of about 5 micron and preferably about 10 micron in thickness. However, both porosity and pressure drop may be balanced in the membrane to maintain desired energy efficiency, so various thicknesses may be similarly utilized to create similar energy efficiency. As formed herein, the ePTFE membrane is filled with a number of large nodes and fine fibrils which allow for tolerance of low concentrations of PAO, DOP, DEHS or other test aerosols. It is believed that the larger diameter fibrils and nodes are more resilient to bleed through of the challenge material such as PAO as the larger diameter fibrils are relatively less affected by equivalent volumes of the oil aerosol.

Figure 14:
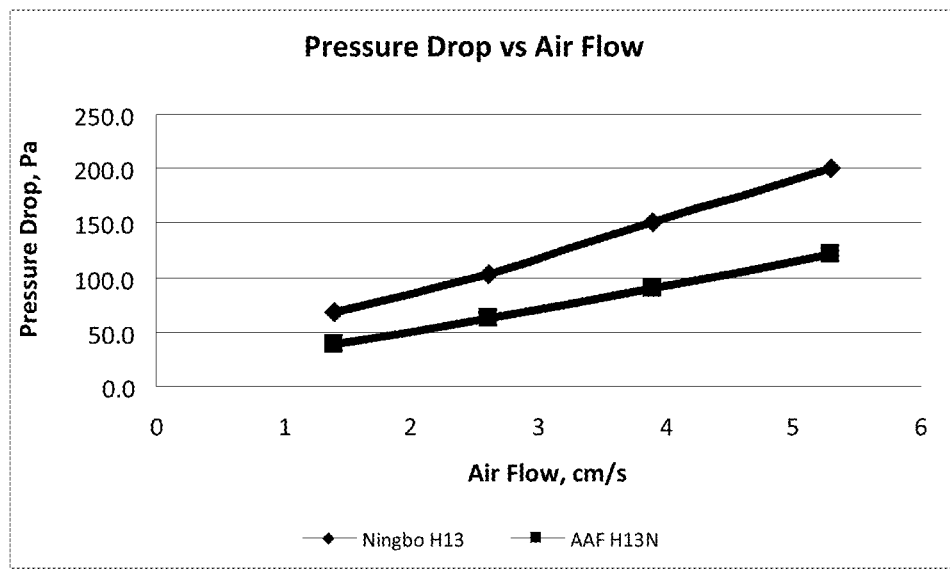
FIG. 14 is a chart illustrating pressure drop versus air flow.
Figure 15:
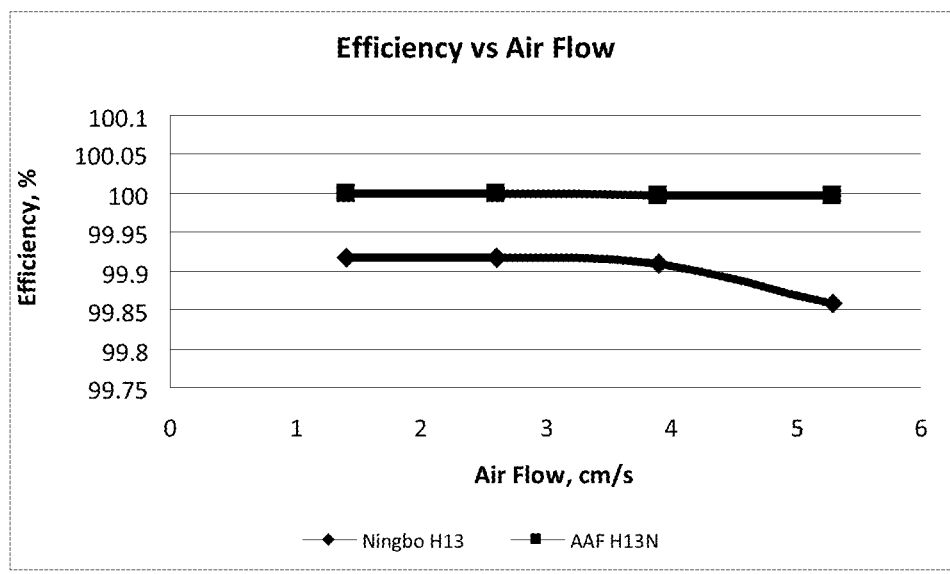
FIG. 15 is a chart illustrating efficiency versus air flow.

As shown in FIG. 14 and FIG. 15 (wherein the triangular dotted line represents a prior art Ningbo (Chinese manufacturer) H13 HEPA filtering media and the square dotted line represents an exemplary embodiment of a HEPA ePTFE dual layer scrim material described herein), the combined ePTFE membrane and scrim material exhibits significant beneficial pressure drop and efficiency characteristics as compared to other known HEPA ePTFE filtering media.

Figure 4:
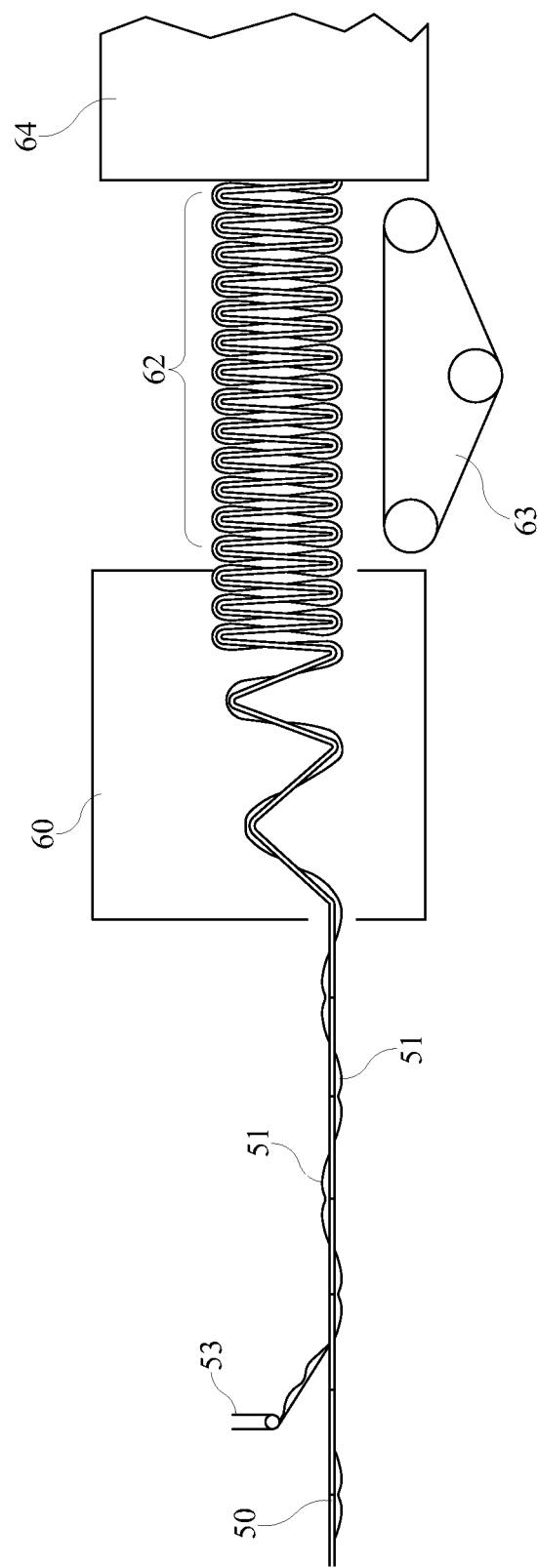
FIG. 4 is an exemplary pleating machine used in making pleated filters according to one aspect of the present invention.
Figure 5A:
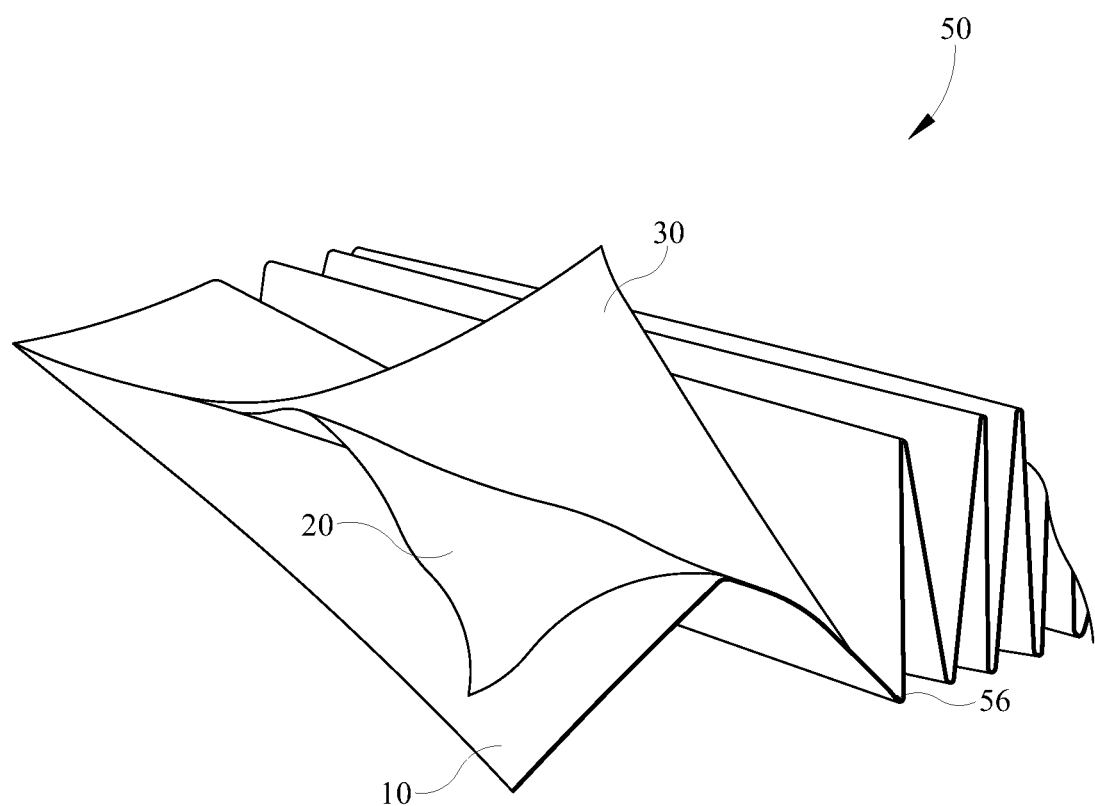
FIG. 5A is a perspective view of a sample sheet of a pleated filter media with one embodiment of a spacer as set forth herein.
Figure 5B:
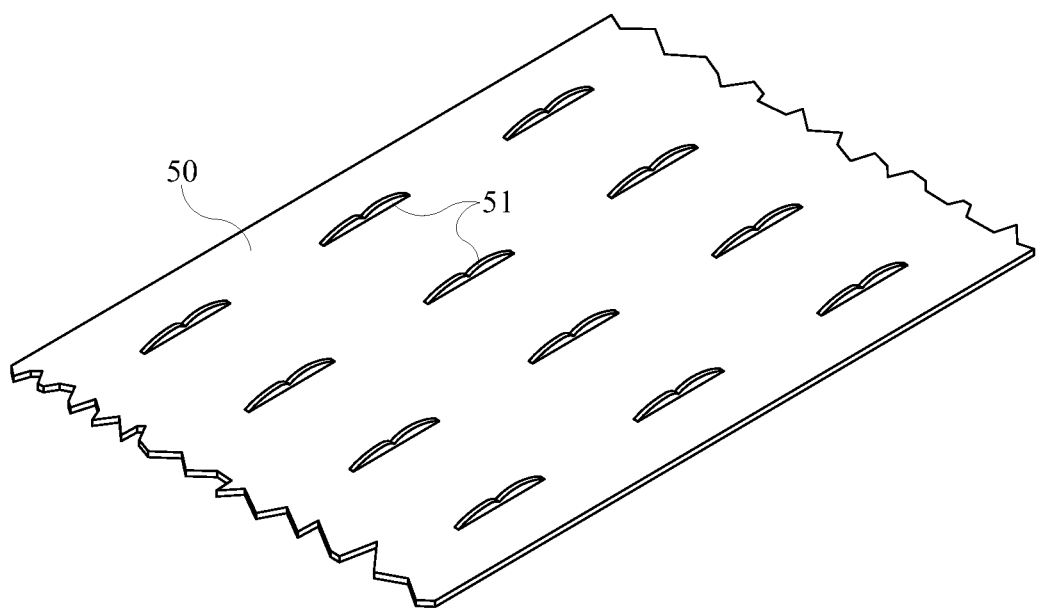
FIG. 5B is a perspective view of a sample sheet of a pleated filter media with an alternative embodiment of a spacer as set forth herein.
Figure 5C:
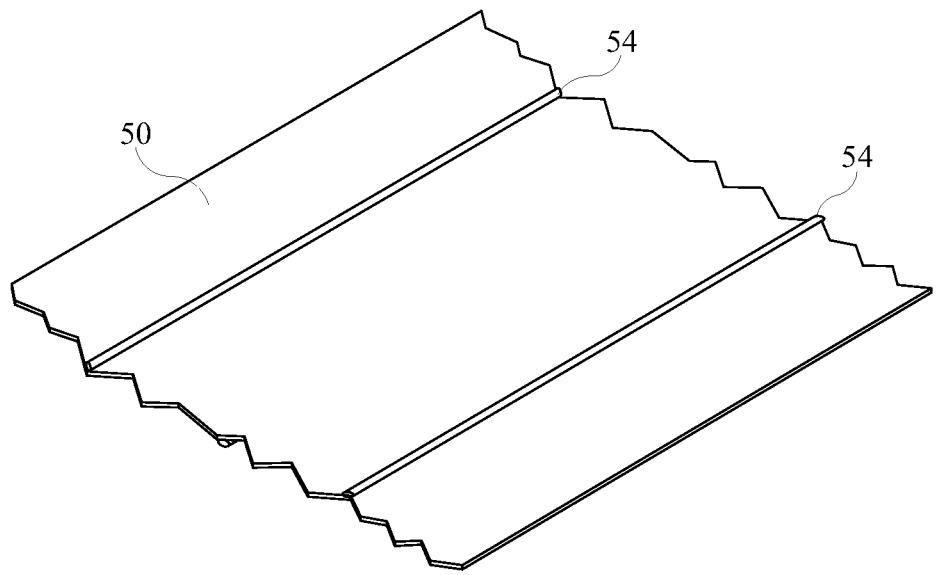
FIG. 5C is a perspective view of a sample sheet of a pleated filter media with a further alternative embodiment of a spacer as set forth herein.

Referring now to FIG. 4, the combined laminated media 50 is prepared for pleating by initially unrolling the combined media and feeding to a belt for conveyance to a pleating apparatus 60. As is understood, pleating is accomplished through many processes and the one depicted is only provided as a means to describe one of a number of processes for pleating, crimping, and folding the ePTFE pleated filter media. Further, the depiction shown in the figures is for descriptive and explanatory purposes. Prior to pleating of the media 50, an injector nozzle 53 provides separator material 51 on the filter media which are used to ensure proper separation of adjacent pleats formed from the media by the pleating machine. Failure to sufficiently separate the pleats can cause the pleats to collapse under the pressure of active airflow. By providing spaced separators, maintenance of the pleat structure is assured to allow for adequate surface area of the filtering media, pleat positioning and efficacy.

Separators 51, depicted in several embodiments of FIGS. 4, 5B, 5C, 6A and 6B, may be of many types of construction. This includes simple beads, sections, bow tie structures, elongated lines 54 or other configurations. Many variations of separator construction may be utilized in order to assure proper pleat position and separation, including embossing the media and even using hot melt to secure the media in place. Separators may also include mechanical separators and spacers as well as bead type separators. The disclosure herein of the multiple separators is provided for exemplary purposes and no unnecessary limitation of such disclosure is to be construed as the teachings hereof are considered to cover equivalent structure for separator functionality.

Figure 6A:
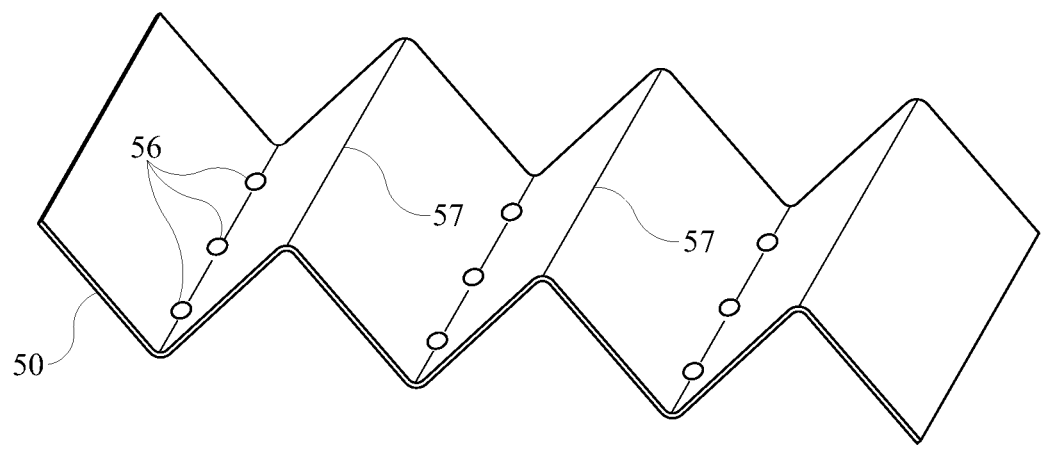
FIG. 6A is an upper perspective view of a sample sheet of a pleated filter media having individual spacer materials inserted into the filter pleats as described herein.
Figure 6B:
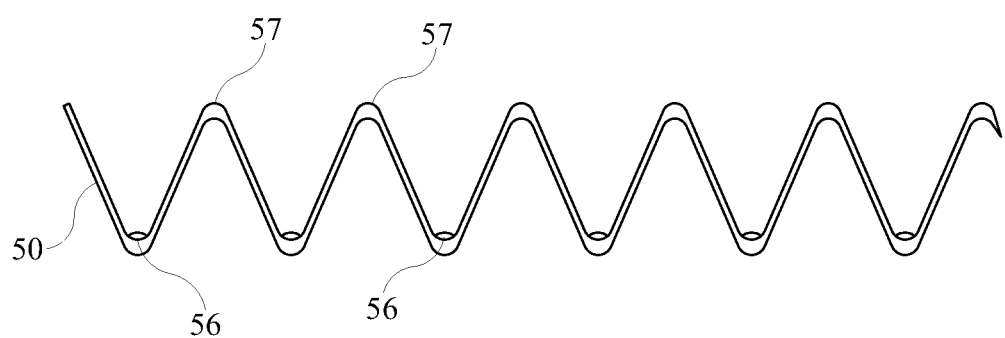
FIG. 6B is a side view of the sample sheet of FIG. 6A.

Bead type separators 56, shown in FIGS. 6A and 6B, are positioned along opposite fold lines 57 to ensure proper pleat positioning. The separators are of a preselected chemistry and quantity in accordance with the geometry and material composition of the filter media, namely size, weight, depth, and breadth. Such separators are positioned so that the opposite pleat faces forming the pleat valleys are spread and maintained a desired preselected position with the valleys being unrestricted for free flow of the fluid stream through the pleated media.

In many embodiments, the separator material may be a clear material which does not interact with the PAO or other challenging aerosol used in the certification challenging steps described herein. For example, the separator material may be poly-alpha olefin which is clear and which does not discolor the adjacent ePTFE media when exposed to PAO oil aerosol.

Returning to FIGS. 4, 5B, 5C, 6A and 6B, the material is folded by a pleating apparatus 60 via many known mechanisms such as using scoring and crimping rollers as are known. A plurality of pleats 62 are created and back plate 64 maintains compressive pressure on the newly pleated filtering media. A pleating conveyor 63 advances the pleated material towards the back plate while the plate expands to accept oncoming additional filtering media.

Figure 7:
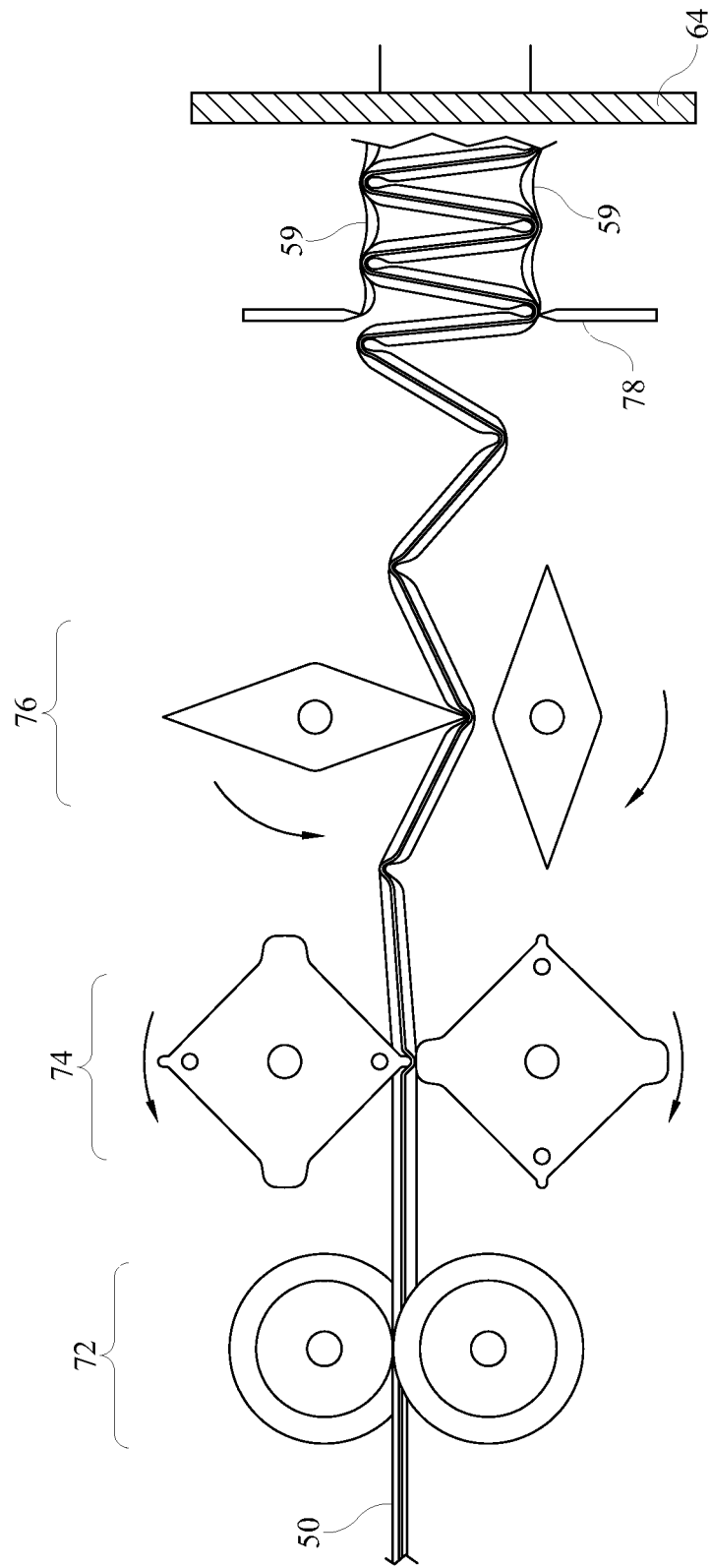
FIG. 7 is a side view of one embodiment for machinery which pleats various embodiments of the filter media described herein.

As shown in exemplary fashion in FIG. 7, the pressure rollers 72 may be combined with the scoring rollers 74 and pleating rollers 76 to properly form the plurality of pleats 62 described. A nozzle 78 may be provided as depicted to position a continuous line of separator material 59 on the tip portion of each pleat in order to maintain proper pleat separation. As indicated, separator material may be a clear poly-alpha olefin which does not leach colors or discolor the white filtering media when exposed to the PAO during the challenging process.

Figure 9:
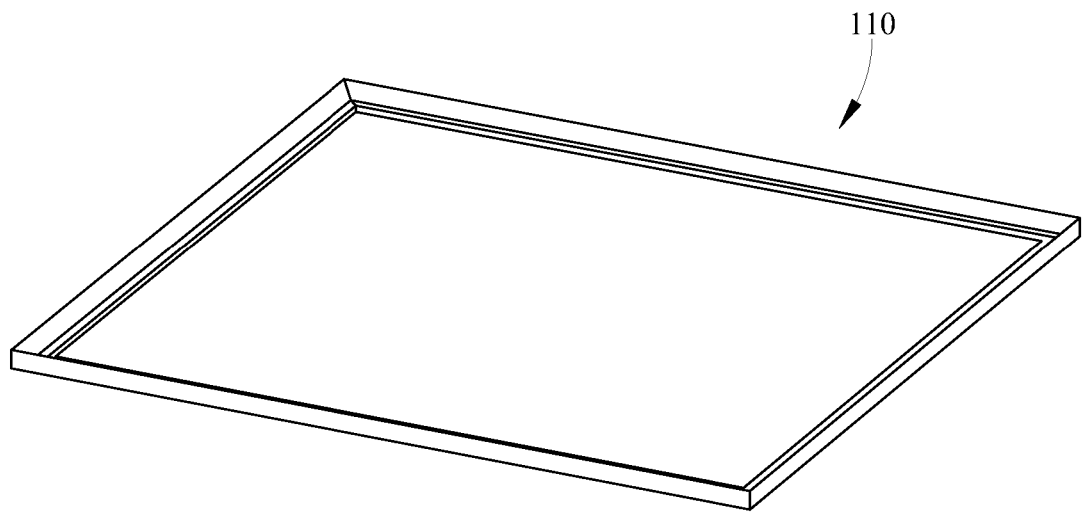

Once the media is properly pleated, it may be cut and prepared for insertion into a frame material 110 as shown in FIG. 9. The filter frame may be anodized extruded aluminum, for example. In some applications, the filter frame, whether utilizing aluminum or a viable alternative as are known, may form a continuous channel that is filled with a non-flowing gel. A skirt or edge 101 may be embedded into the gel sealant to effect a leak-proof seal between the filter install environment. Alternatively, a gasket seal system may be utilized wherein a flat flange on the downstream side of the filter frame is implemented. Other known frame structures and seals may be utilized in the various embodiments disclosed. Gel seals may also be utilized which, in various installations, may include an elastomeric.

Figure 8:
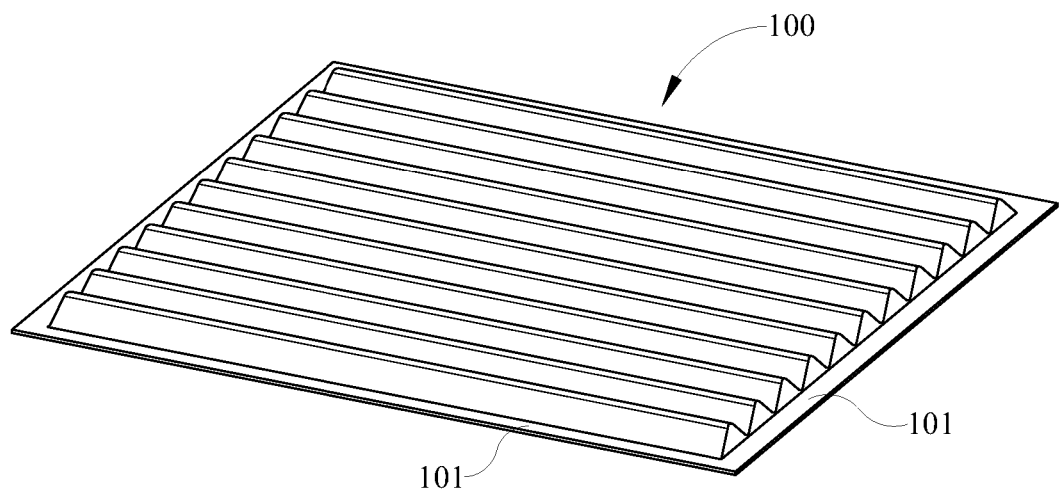
FIGS. 8 and 9 are perspective views of a pleated filter media prepared for insertion in a frame and a view of an exemplary frame for holding same.
Figure 10:
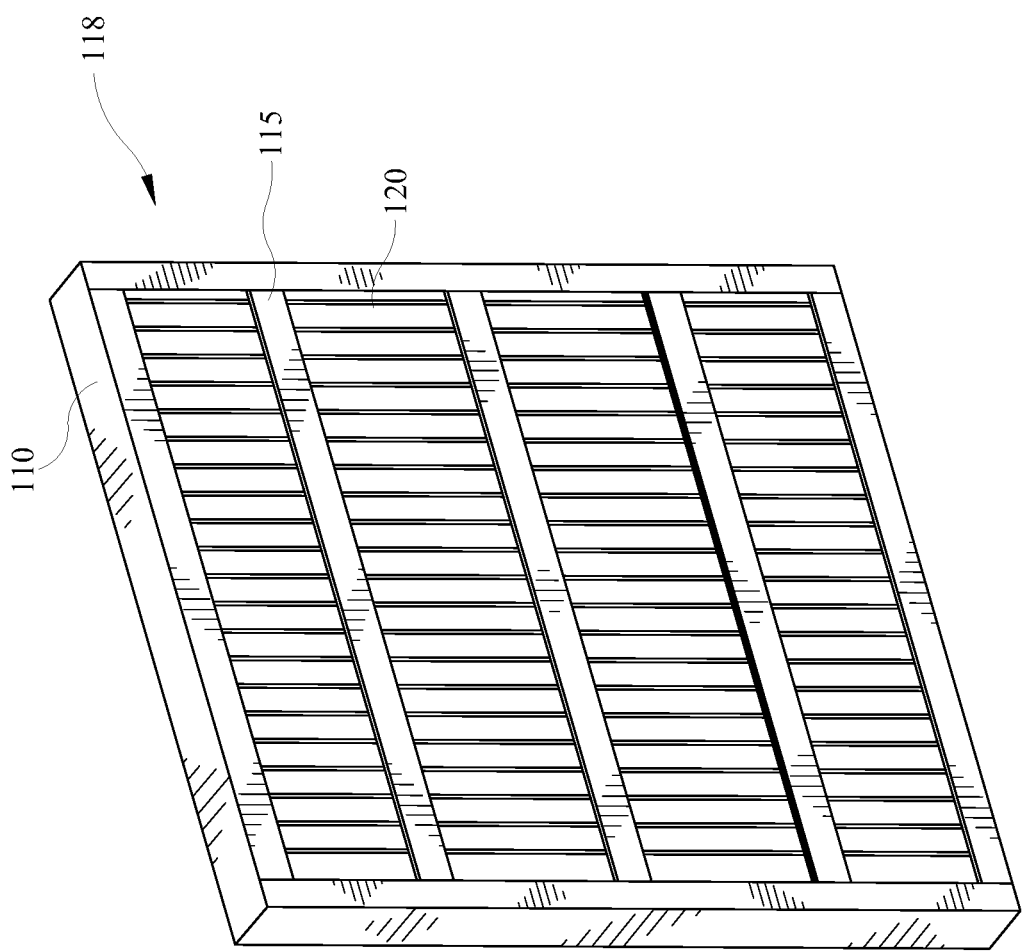
FIG. 10 is a perspective view of the assembled filtering media and frame combined for use according to one aspect of the present invention.

A single filter unit 100 is shown in FIG. 8 prior to insertion into a frame structure 110. Edges 101 may be crimped for retention within the frame structure, the entire filter retained within the structure by known method and structures available. FIG. 10 depicts an exemplary embodiment in which the completed filter 118 includes exemplary support strips 115 with a plurality of pleats 120 shown and properly supported by various separator structure as described.

After installation into an aseptic pharmaceutical facility, in place certification must be conducted. As discussed herein, such challenging often includes challenging with an oil based aerosol such as PAO in order to determine leak size and filter structural continuity. In combination with the ePTFE filtering media set forth, a process is provided for ultra-low concentration challenging of filtering media in an aseptic pharmaceutical environment. In general and in various embodiments described herein, one or more ePTFE filter embodiments described herein may be utilized in an ultra-low aerosol concentration challenging step wherein the upstream airflow is entrained with a challenging compound. In general and in various aspects set forth, PAO aerosol may be introduced upstream in order to determine damage to the filter or seal structure. Such normal and periodic leak determination and examination is required in such applications and through use of the ultra-low concentration methodology in combination with the ePTFE filter, filter life can be significantly enhanced up to and including the lifespan of the facility.

Figure 11:
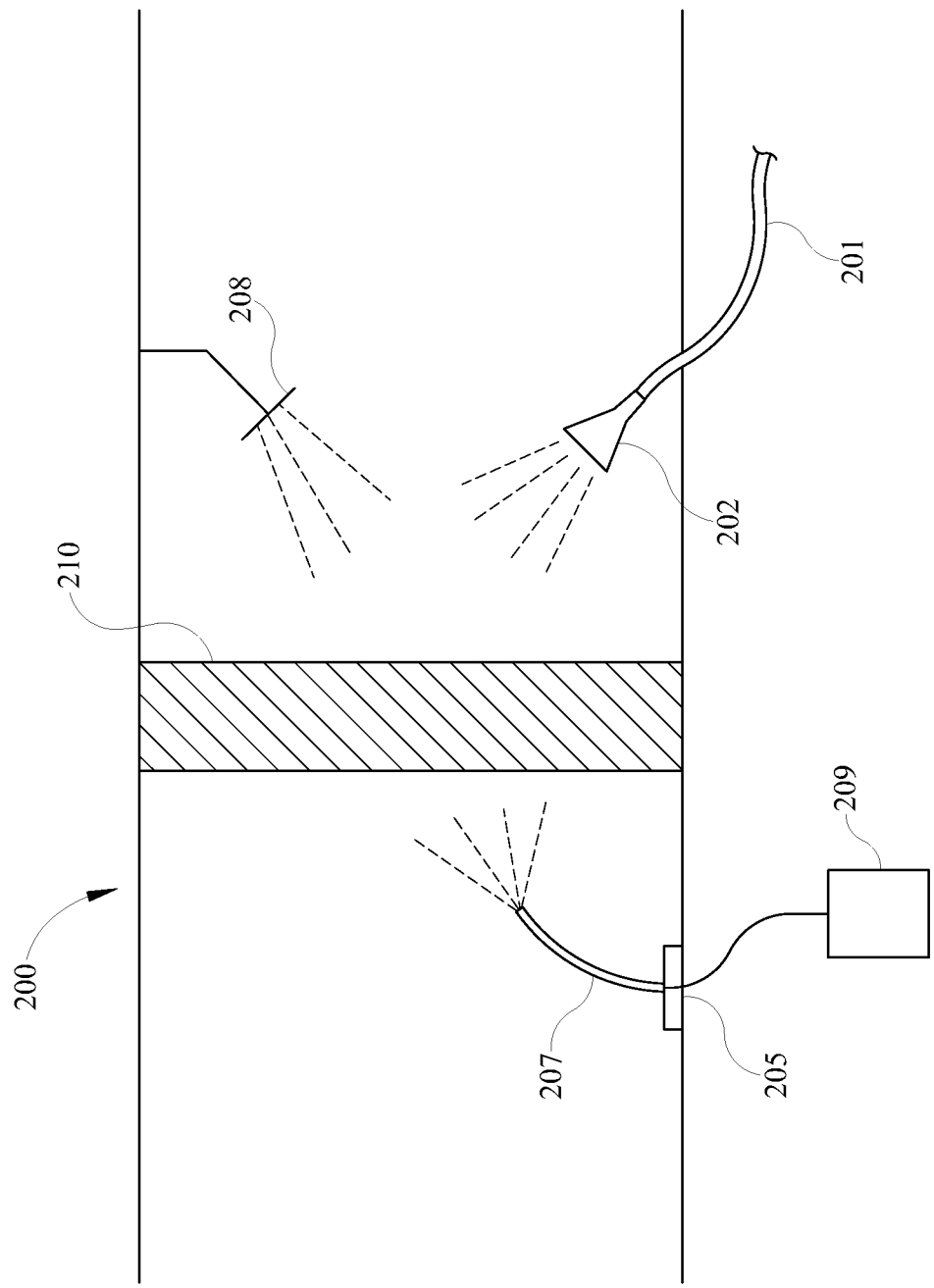
FIG. 11 is a side sectional view of a representative aseptic pharmaceutical installation using an ePTFE filter and a challenge configuration.

In general, and as is depicted by example only in FIG. 11, an ePTFE filter 210 is placed within an airstream within duct or other air conveyance system 200. During challenging of the ePTFE media, a source of ultra-low concentration of PAO or other aerosol is placed upstream of the filter 210. In this embodiment, a modified Laskin nozzle 202 having a supply 201 may be operational as a low or ultra-low volume emitter of challenging aerosol. In certifying such filters, leakage is determined by comparison of the challenge concentrations at both the upstream side versus the downstream side. If a leak or other structural imperfection in the filtering media and filter seal is present, downstream concentrations of greater than about 0.01% indicates such. Thus, upstream and downstream concentrations of the challenging material must be determined, and a concentration calculated. Alternative aerosol generation may be accomplished such as thermal condensation type aerosol generator or other known systems that are available for such concentration aerosol generation. These systems may be utilized in order to implement the filter penetration method described herein.

In some of the embodiments discussed, a challenging material such as PAO aerosol may be utilized. As a result of installing a HEPA ePTFE filtering media in one example, ultra-low concentrations of the PAO may be introduced using an aerosol generator and diluter which may be combined, as depicted for exemplary purposes in FIG. 13, or separated within the challenge mixing air supply and duct, as needed. These low and ultra-low concentrations are suggested to range between about 1.0 µg/L down to about 0.01 µg/L. Such small concentrations on the downstream side of an ePTFE filtering media require discrete measurements of particles. Thus, a discrete particle counter 209 may be utilized to accurately measure such ultra-low concentrations of the challenging material. As shown, a particle counter 209 may be combined with a hand scan probe or other discrete measurement device 207 which can be fed into the downstream airflow adjacent to the downstream side of the filter 210 via an access port 205 to take appropriate measurements.

Downstream concentration measurements by the particle counter 209 may be compared to upstream concentrations calculated by the upstream scanner 208 in order to determine PAO penetration concentrations. As indicated, downstream concentrations of greater than about 0.01% of upstream concentrations would indicate filter integrity issues. And, as a result of embodiments using a HEPA ePTFE media, only ultra-low concentrations of the challenging PAO aerosol can be utilized in order to avoid fouling the media or otherwise resulting in a significant drop in efficiency and filtration capability. As such, specialized ultra-low concentration measuring protocols and equipment must be utilized to determine downstream concentrations and leakage percentage.

Referring again to FIG. 11, as indicated above, it is significantly desirable to use the various embodiments of filtering media disclosed herein as compared to traditional micro-glass. As a result, such methodology using ultra-low concentration generators of aerosol must be used in combination with detection equipment of such concentrations at both the upstream and downstream side of the media 210. An upstream scanner 208 may be combined with the downstream scanner 209 as shown. Automated systems including a microprocessor and software may be utilized to read the measurements of the two scanning devices in order to quickly and accurately determine downstream concentrations. Such microprocessor may be incorporated with said upstream scanner, downstream scanner, or in some embodiments, may combine both structures and functionality to calculate the downstream leakage percentage. Alternatively, in other embodiments, downstream measurements may be made and determinations of downstream ultra-low concentrations then determined.

Upstream concentrations, even when at ultra-low values as specified herein, may be so large that an upstream discrete particle counter may be overwhelmed. Thus, in some embodiments, a combination of an upstream photometric scanner with a downstream discrete particle counter may be utilized in order to calculate the appropriate downstream penetration percentage concentration of the challenging aerosol. In general, an upstream aerosol photometer with an associated filter scanning head 208 may be used to determine ultra-low upstream concentrations. Associated with the upstream aerosol photometer and scanning head 208 may be a modified Laskin nozzle 202 which generates the ultra-low concentrations of the challenge PAO for the filter test and certification. Such Laskin nozzle generator may be used in combination with an aerosol reducer such as an oil mist eliminator with an 18-gauge capillary bypass. The modified Laskin aerosol generator may be modified such that finite control and output of the challenge PAO concentrations may be maintained at such low concentrations as to not substantially affect the efficiency and effectiveness of the HEPA ePTFE filtration media 210 depicted. Such concentrations include controllable emissions of from about 1.0 µg/L down to about 0.01 µg PAO/L or lower which may include determination of concentrations down to about 0.3 µm/cubic foot or about 6 million particles per cubic foot or lower. Of course, the upstream detector 208 may be any type of ultra-low concentration detectors capable of accurately measuring the PAO concentrations on the upstream airflow and filter face such that an accurate calculation of the downstream concentration percentage may be made.

Associated with the modified Laskin nozzle 202 and aerosol reducer and upstream detector 208 is a downstream detector which must be capable of measurements as low as 0.01% of the ultra-low upstream concentrations. Thus, an exemplary laser particle counter 209 with a rectangular hand scan probe, as one example embodiment, may be utilized in order to scan the filter corners and having a 0.3 µm particles or smaller minimum detectable size and concentration and a rectangular hand scan probe to fulfill near isokinetic flow conditions.

For example, in some embodiments, a flow-thru system with sheath flow, multi-LED and/or laser diode for excitation may be used. Such associated electronics will utilize scattering for detection and should be capable for detection of particle sizes down to 0.1 µm and mass concentration of about 1 µg/L down to 0.01 µg/L or lower for use of a photodiode or discrete particle detector. Further, for very low concentrations, near particle counter detection may be utilized with mass aerosol at a minimum of 0.1 µm and larger (i.e. particle counter/photometer with the capability to measure the penetration of 0.01% when the upstream concentration is 0.01 µg/L and greater). As indicated, a processor may be integrated into the interfacing for auto-calculating particle counting into penetration of the filtering media to determine leakage.

Once known upstream and downstream concentrations are calculated, a leak rate calculation may be completed wherein the upstream concentration is divided into the downstream concentration to determine the leakage rate. Calculations as low as a value equal to or greater than 0.01% challenge concentrations downstream would indicate a leak within the filter or seal structure. Automated leak calculation may be implemented by electronically connecting the upstream scanner 208 and the downstream scanner 209 such that leakage rates which compare the two scans may be determined. Such electronic connection may be standard communication lines between the devices, electronic communication lines between a centralized computer which reads the data from each device and provides automated leakage calculation, or an integrated scanning device which is capable of interconnected upstream and downstream measurements and which, after a specified exposure time period, calculates the appropriate downstream concentrations and the leakage values.

Exemplars

An exemplary measurement test was conducted on the effects of ultra low (<0.3 mg/m3 (µg/L)) PAO concentration testing of ePTFE filters was performed. The study showed the equivalence and effectiveness of testing ePTFE filters with industry typical concentrations (10 mg/m3 (µg/L) or greater) and ultra low concentrations of PAO to detect leaks and determine their sizes.

The conventional test method of using a photometer and a ≥10 mg/m3 (µg/L) PAO challenge was employed as a means to size defects created in an ePTFE filter. The results were directly compared to an alternative test method that was composed of using a discrete particle counter (DPC) with ultra-low reduced (<0.3 mg/m3 (µg/L)) PAO challenge concentrations. Testing was performed by creating twelve defects in a HEPA filter of a LFH (Laminar Flow Hood). Comparative test data was then taken using the two methods. The testing construction is shown in FIG. 13.

An X-Y axis linear bearing sample probe positioning device was placed in front of the LFH as a means to remove sampling variation due to probe positioning. This unit consisted of a base secured on the floor, with movable horizontal and vertical axes for exact probe positioning.

Figure 13:
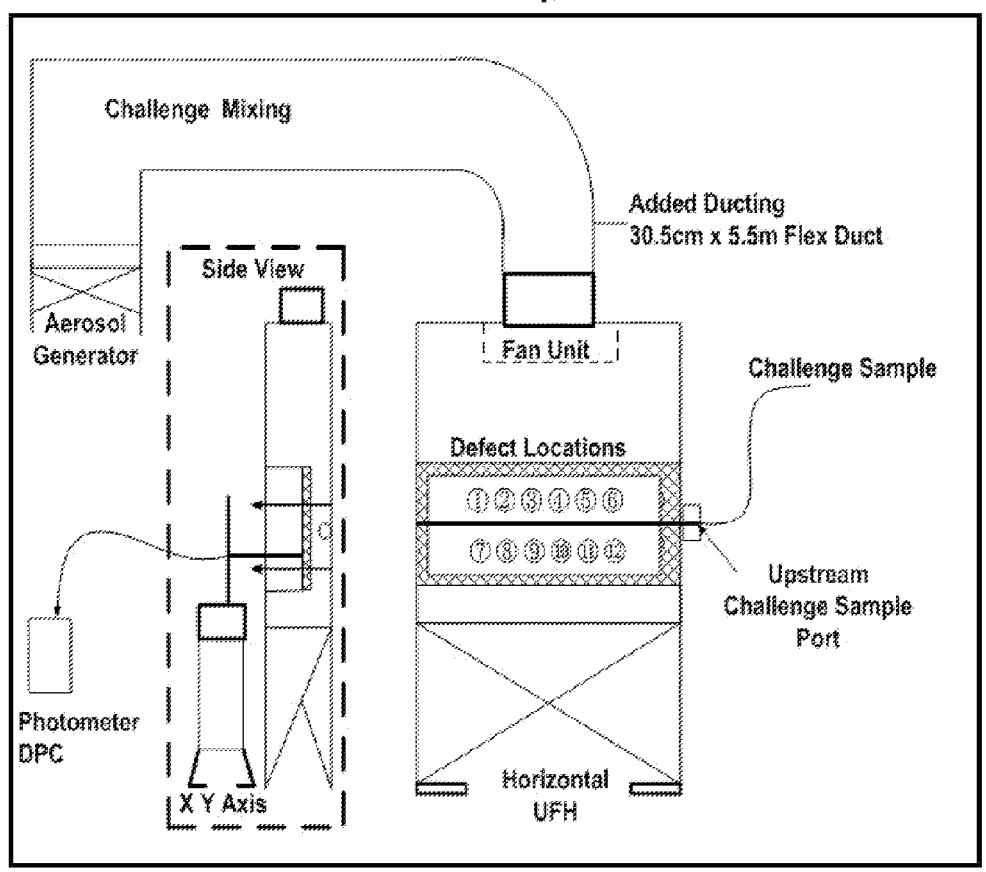
FIG. 13 is a testing machine for determination of ultra-low concentrations of challenging aerosol using the system and method of the present invention.

The exemplar was performed using a 610 mm×1220 mm (2 ft×4 ft) horizontal LFH as shown and depicted in FIG. 13. A HEPA filter used for the study was an ePTFE filter as disclosed herein rated for a nominal flow of 630 cfm with an efficiency rating of 99.95% at the MPPS (Most Penetrating Particle Size). The LFH was tested for airflow velocity, leaks, and unidirectional flow prior to beginning the study. Determination of the uniformity of the aerosol challenge was accomplished by fabricating and installing a stainless steel guide upstream of the filter. A sampling tube was then inserted into the guide and positioned so the sample tube opening was located at the end of the guide. A flex duct was attached (30.5 cm (12 in.) diameter×5.5 m (18 ft)) to the inlet of the hood to achieve adequate upstream mixing.

Measurement and test equipment utilized to determine aerosol challenge concentrations upstream of the testing ePTFE HEPA filter was a TSI 2-G photometer and a Lighthouse Solair model 3100 laser particle counter in combination with a Milholland & Associates model 450ADS aerosol diluter as listed in Table 1 below. The particle counter and diluter instrument combination was used to determine the actual number of challenge particles for ultra low level PAO testing (<0.3 mg/m3 (µg/L) which corresponds to conditions 1 and 2 set forth in Table 1.

Study Conditions

The equipment and materials utilized in this sample test included the following: Discrete Particle Counter; Portable Self-Contained Aerosol Generator; Poly-alpha-olefin (PAO); Photometer; 2'×4' Horizontal Laminar Flow Hood; Aerosol Dilutor; X-Y Axis Positioning Device; 12"×18' Flexible Ducting; Air Data Multimeter; Handheld Ultrasonic Aneometer. Three evaluated conditions were derived from a combination of the particle sizes (0.3 and 0.5 µm), photometer and DPC test equipment, and the selected aerosol challenge concentrations (PAO). The following table Table 1 defines the test instruments, concentrations, and particle sizes tested. A PAO aerosol produced by a Laskin nozzle of 38 million particles>0.3 µm is equivalent to approximately 0.1 mg/m3 (µg/L).

TABLE 1

| Method | Condition | Instrument | Reported Challenge Measurements |
|---|---|---|---|
| Ultra Low PAO | 1 | Discrete Particle Counter | ~20 × 10$^6$ ≥ 0.3 µm particles per ft$^3$ PAO |
|  | 2 | Discrete Particle Counter | ~7 × 10$^6$ ≥ 0.5 µm particles per ft$^3$ PAO |
| Standard PAO | 3 | Aerosol Photometer | >11 mg/m$^3$ (µg/L) |

Defects consisting of twelve holes were made in the ePTFE media by inserting a 30 gauge hypodermic needle into the media twice at each defect site. The average face velocity of 104 fpm (192 m/sec) was determined using the ultrasonic anemometer. The face area of the filter was 6.52 ft2. The volumetric flow through the filter was calculated to be 675 cfm. Pressure drop across the filter was measured to be 0.158" wc. It was noted this was approximately 25% of the pressure drop of a comparable wet-laid microglass filter (0.58" wc @650 cfm) operating at 90% of the airflow volume of ePTFE.

Upstream mixing was verified using a particle counter with ultra low concentrations of PAO as the challenge. Measurements were taken at six locations upstream of the ePTFE filter. The sample locations fell in between the two rows where the defects were created, that being approximately four inches below and above the first and second rows respectively. The PAO sample reading variance for the six locations was less than about 1%.

TABLE 2

Upstream particle counts at leak detection points

| Sample Location | counts/ft$^3$ ≥0.3 micron particles | counts/ft$^3$ ≥0.5 micron particles |
|---|---|---|
| 1 | 37890 | 11224 |
| 2 | 39732 | 12038 |
| 3 | 39726 | 12018 |
| 4 | 39484 | 11868 |
| 5 | 39624 | 12114 |
| 6 | 38626 | 11810 |

A quarter-sized Laskin nozzle generator was used in combination with an aerosol reducer (oil mist eliminator with an 18 gauge capillary bypass) to provide the upstream challenge. Thirty-second samples (0.5 ft$^3$) were taken at each of the six locations and the counts per cubic foot are shown above. The differential pressure of the dilutor was measured at 4.89" we which corresponded to a dilution factor of 966. The Laskin nozzle generator with the aerosol reducer created a filter challenge of approximately 20 million particles at ≥0.3 µm and approximately 7 million particles at ≥0.5 micron per cubic foot of air. The sizing was repeated 10 times to gain statistical significance.

Ultra Low PAO<0.3 mg/m3 (µg/L) Challenge Using a Discrete Particle Counter (Conditions 1 and 2)

The ePTFE Filter was challenged with an ultra low level of PAO in the range of 0.3 mg/m3 (µg/L), as determined by the photometer. The defect sizes were measured in order starting with defect 1 and continuing sequentially to defect 12. After completing the defect sizing, a new upstream challenge was measured and defect sizing was repeated for a total of 10 runs to give statistically valid numbers.

At the beginning and end of each run the upstream challenge was recorded. At the end of run 8 it was noted that the upstream challenge was increasing at a significant rate. It was theorized that the increase was related to loading of the oil mist eliminator used to reduce the output of the aerosol generator. Runs 9 and 10 were excluded in the analysis due to the abruptly rising challenge concentrations. The rising concentrations affect the dilution and therefore the downstream counts of the particle counter regardless of the material being tested so it was determined to be a mechanical flaw.

Standard PAO 10.0 mg/m3 (µg/L) Challenge Using an Aerosol Photometer (Condition 3)

The third condition consisted of utilizing the traditional PAO aerosol/photometer method to size the defects created in the ePTFE filter. The ePTFE filter was challenged with approximately 10.7 mg/m3 (µg/L) (average upstream of 10 runs) of PAO using a TEC 1.5 Laskin nozzle generator operating at 20 psi. The defect sizes were measured with a photometer in order starting with defect #1 and continuing sequentially to defect #12. After completing sizing for all 12 defects, a new upstream challenge was measured and defect sizing was repeated for a total of 10 runs. The average (over 10 runs) defect size is shown below for each defect 1-12.

SUMMARY

The performance of the ePTFE was unaffected during testing. The data showed that the ePTFE filter was unaffected by the testing as it maintained efficiency of at least 99.99% and a pressure drop of 0.1578" H2O. This is compared to a capture efficiency of 99.99% and a 0.6" H2O pressure drop across the glass filter at 90% of the airflow.

Figure 16:
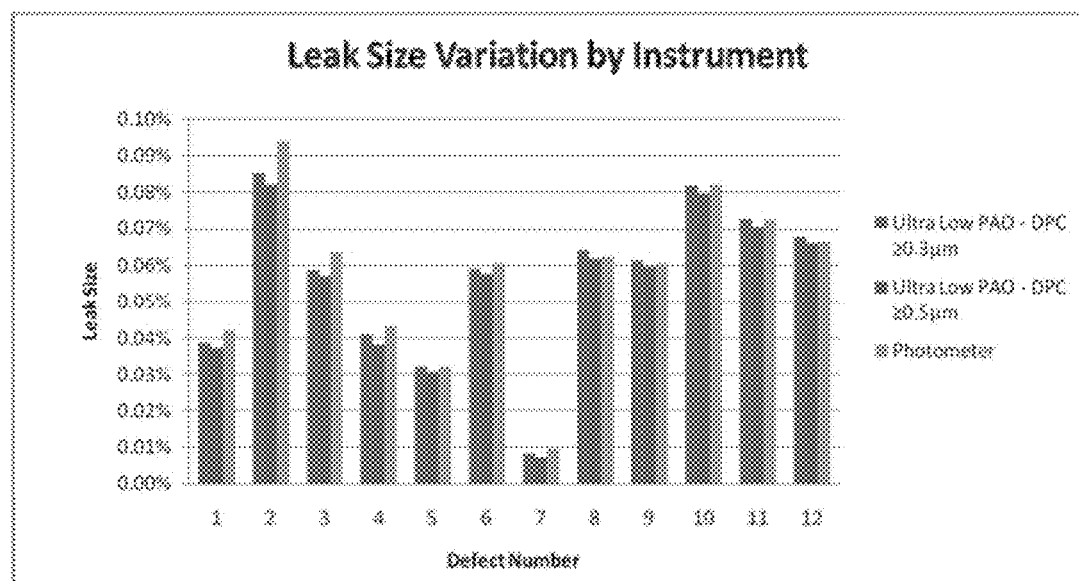
FIG. 16 is a chart illustrating leak size variation by instrument.

The average leak sizes for the three test conditions are shown in FIG. 16. A direct comparison of the test method reveals that the particle counter on average sized the leaks slightly smaller than the photometer for both the ≥0.3 μm and ≥0.5 μm particle size distribution conditions. To better understand the repeatability and reproducibility of the measurement and test equipment used in this example, a head-to-head leak size comparison using 10 photometers was carried out. The same comparison was later carried out using 7 particle counters. The results of the study showed that there was no statistical difference between the leak sizes obtained for the standard high concentration and ultra low concentrations and test methods presented.

It was noted that the particle counter on average sized leaks slightly larger than the photometer. To better understand the repeatability and reproducibility of the measurement and test equipment used in the study, a head to head leak size comparison using 10 photometers was carried out. The same comparison was later carried out using 7 particle counters. The results of the study showed that there was no statistical difference between the leak sizes obtained for the traditional and ultra-low concentration methods.

Two test methods were employed to size defects in an ePTFE filter.

Ultra low level (~0.3 μg/l) PAO challenge with a discrete particle counter

Standard level (~10 μg/l) PAO challenge with a photometer. The results indicate that defects in the ePTFE filter can accurately be sized using ultra low level PAO challenges and a particle counter. Under the aforementioned test methods, both DPC test options (≥0.3 μm and ≥0.5 μm particle count defect sizing) performed adequate in comparison to the photometer.

The variation of sizing leaks with a discrete particle counter as set forth in the method herein falls within the variation of the individual photometer tested. The results provide validity to utilizing low PAO concentrations and DPC's to determine leak size in ePTFE filters. Utilizing this methodology, the loading of the filter will take 150-300 times as long based on previous testing.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An ePTFE filtering media and challenge testing configuration for an in-situ pharmaceutical installation of the filtering media, comprising:
    a pleated filtering media positioned within an air stream of an air handling unit in an aseptic pharmaceutical airstream handling system, said filtering media including an upstream support scrim and a downstream support scrim and an ePTFE membrane interposed between said upstream support scrim and said downstream support scrim;
    wherein said upstream support scrim and said downstream support scrim are a bi-component material and said ePTFE membrane is laminated therebetween;
a poly-alpha olefin separator between of each of said plurality of pleats of said pleated filtering media;
    an upstream low volume aerosol generator combined with an aerosol diluter providing less than 0.3 μg aerosol/L air down to 0.01 μg aerosol/L air and below for ultra-low volumes of aerosol concentrations into said air stream of said air handling unit;
    an upstream scanner for detection of the aerosol concentrations for ultra-low volumes at said upstream support scrim of said filtering media;
    a downstream scanner with a scanning probe inserted into said air handling unit downstream of said pleated filtering media and facing said downstream support scrim, said scanning probe inserted through an access port in said air handling unit of said pharmaceutical airstream handling system for detection of the aerosol concentrations for ultra-low volumes passing through said downstream support scrim of down to 0.01 percent of the aerosol concentrations for ultra-low volumes detected at said upstream scanner.

2. The configuration of claim 1 wherein said downstream scanner is operable to detect the aerosol concentrations for ultra-low volumes passing through said downstream support scrim as low as 0.000001 μg aerosol/L air.

3. The configuration of claim 2 wherein said downstream scanner is a discrete particle scanner.

4. The configuration of claim 1 wherein said upstream low volume aerosol generator is a modified laskin nozzle generator in combination with said aerosol diluter being an oil mist eliminator having an 18 gauge capillary bypass creating a dilution factor of 960.

5. The configuration of claim 1 further comprising an electrical communication between said upstream scanner and said downstream scanner.

6. The configuration of claim 5 further including a microprocessor in communication relationship with both said upstream scanner and said downstream scanner.

7. The configuration of claim 1 wherein said pleated filter media is a HEPA filter.

8. A method for installation and leakage testing of ePTFE filtration media in an in-situ aseptic pharmaceutical filtration environment, comprising:
    installing a filtration media in an aseptic pharmaceutical filtration environment, wherein said filtration media has an upstream spun bond scrim material and a downstream spun bond scrim material;
    interposing an ePTFE membrane between said upstream spun bond scrim material and said downstream spun bond scrim material;
    injecting upstream of said filtration media an ultra-low concentration of oil based aerosol of below 0.05 μg aerosol/L air;
    diluting said aerosol with an aerosol reducer to a dilution factor of between 750 to 1000;
    creating an ultra-low filter challenge concentration of 20 million particles at greater than or equal to 0.3 micron and 7 million particles at greater than or equal to 0.5 micron per cubic foot of air;
    measuring an upstream concentration of said oil based aerosol at said upstream spun bond scrim material;
    allowing said oil based aerosol to penetrate through said ePTFE membrane;
    measuring a downstream concentration of said oil based aerosol by particle detection at said downstream spun bond scrim material to a value at least as low as 0.01 percent of said upstream concentration at said upstream spun bond scrim material;
    calculating a leakage detection of said oil based aerosol.

9. The method for installation and leakage testing of ePTFE filtration media of claim 8 wherein said method further comprises installing an upstream scanner for said measuring said upstream concentration of said oil based aerosol at said upstream spun bond scrim material; installing a downstream particle scanner for said measuring said downstream concentrations of said oil based aerosol at said downstream spun bond scrim material.

10. The method for installation and leakage testing of ePTFE filtration media of claim 9 further comprising transmitting said upstream concentration measurements of said upstream scanner to a computer; transmitting said downstream concentration of measurements of said downstream scanner to a computer; calculating a leakage percentage of said oil based aerosol through said ePTFE filtration media over a predetermined period of time.

11. The method for installation and leakage testing of ePTFE filtration media of claim 8 further comprising:
    installing a communication link between an upstream scanner and a downstream scanner;
    transmitting said upstream concentration measurements of said upstream scanner to a reading device;
    transmitting said downstream concentration measurements of said downstream scanner to said reading device;
    calculating a leakage percentage of said oil based aerosol through said ePTFE media by a processor;
    reporting said calculated percentage to a user.

12. The method for installation and leakage testing of ePTFE filtration media of claim 8 wherein said method further comprises installing an upstream photometric scanner for measuring said upstream concentration of said oil based aerosol at said upstream spun bond scrim material and installing a downstream particle detection scanner for measuring said downstream concentration of said oil based aerosol at said downstream spun bond scrim material.

13. A method for leakage testing of a filtering media in an in-situ aseptic pharmaceutical filtration environment, comprising:
- providing a filtering media in an aseptic pharmaceutical filtration environment, wherein said filtering media includes an ePTFE membrane;
- providing upstream of said filtering media an oil-based aerosol in a range of 0.3 μg aerosol/L air to 0.01 μg aerosol/L air;
- measuring an upstream concentration of said oil-based aerosol upstream of said filtering media;
- measuring a downstream concentration of said oil-based aerosol downstream of said filtering media having passed through a leak in said filtering media to a value at least as low as 0.01 percent of said upstream concentration; and
- calculating a leakage detection of said oil-based aerosol based on a comparison of said upstream concentration and said downstream concentration.

14. The method for leakage testing of a filtering media of claim 13 wherein said filtering media further comprises an upstream support scrim and a downstream support scrim, wherein said ePTFE membrane is interposed between said upstream support scrim and said downstream support scrim.

15. The method for leakage testing of a filtering media of claim 13 wherein the step of measuring said downstream concentration of said oil-based aerosol includes a discrete particle counter.

16. The method for leakage testing of a filtering media of claim 13 wherein said method further comprises installing an upstream scanner for said measuring said upstream concentration of said oil-based aerosol and installing a downstream particle scanner for said measuring said downstream concentration of said oil-based aerosol.

17. The method for leakage testing of a filtering media of claim 13 wherein said method further comprises diluting said oil-based aerosol to said range.

* * * * *